US011318108B2

(12) United States Patent
Moroni et al.

(10) Patent No.: US 11,318,108 B2
(45) Date of Patent: May 3, 2022

(54) USE OF CAROTENOID DERIVATIVES TO REDUCE THE TOXICITY AND INCREASE THE EFFICACY OF ANTI-EGFR ANTITUMOR TREATMENTS

(71) Applicant: ASSOCIAZIONE ONCOLOGICA MILANESE AMO LA VITA ONLUS, Milan (IT)

(72) Inventors: Mauro Moroni, Milan (IT); Paolo Pedrazzoli, Ziano Piacentino (IT); Marco Giulio Giuseppe Pirovano, Milan (IT)

(73) Assignee: ASSOCIAZIONE ONCOLOGICA MILANESE AMO LA VITA ONLUS, Milan (IT)

( * ) Notice: Subject to any disclaimer, the term of this patent is extended or adjusted under 35 U.S.C. 154(b) by 162 days.

(21) Appl. No.: 16/478,915

(22) PCT Filed: Jan. 15, 2018

(86) PCT No.: PCT/IB2018/050229
§ 371 (c)(1),
(2) Date: Jul. 18, 2019

(87) PCT Pub. No.: WO2018/134717
PCT Pub. Date: Jul. 26, 2018

(65) Prior Publication Data
US 2021/0128491 A1 May 6, 2021

(30) Foreign Application Priority Data
Jan. 19, 2017 (IT) .................. 102017000005649

(51) Int. Cl.
| | |
|---|---|
| *A61K 31/01* | (2006.01) |
| *A61K 39/395* | (2006.01) |
| *A61K 45/06* | (2006.01) |
| *C09K 15/00* | (2006.01) |
| *A61P 39/00* | (2006.01) |
| *A61P 35/00* | (2006.01) |
| *A61K 47/42* | (2017.01) |
| *C07K 16/28* | (2006.01) |
| *C07K 16/24* | (2006.01) |

(52) U.S. Cl.
CPC .......... *A61K 31/01* (2013.01); *A61K 39/3955* (2013.01); *A61K 45/06* (2013.01); *A61K 47/42* (2013.01); *A61P 35/00* (2018.01); *A61P 39/00* (2018.01); *C09K 15/00* (2013.01); *A23V 2250/213* (2013.01); *C07K 16/244* (2013.01)

(58) Field of Classification Search
None
See application file for complete search history.

(56) References Cited

U.S. PATENT DOCUMENTS

2011/0190244 A1   8/2011   Zalcberg

FOREIGN PATENT DOCUMENTS

| EP | 0600544 | 6/1994 |
|---|---|---|
| WO | 03041695 | 5/2003 |

OTHER PUBLICATIONS

Harandi et al, Hindawi Publishing Corporation Journal of Oncology vol. 2009, pp. 1-14.*
Carteni et al, Annals of Oncology 18; Supplement 6): vi16-vi21, 2007.*
Starok et al, Biomacromolecules 2015, vol. 16, pp. 1634-1642.*
International Preliminary Report on Patentability issued by the EPO dated Jul. 23, 2019 for International patent application No. PCT/IB2018/050229.
International Search Report issued by the EPO dated Mar. 28, 2018 for International patent application No. PCT/IB2018/050229.
Rafi Mohamed M et al: "Lycopene modulates growth and survival associated genes in prostate cancer", The Journal of Nutritional Biochemistry, val. 24, No. 10, Mar. 2013 (Mar. 2013), pp. 1724-1734, XP028731175.
A. Sartore-Bianchi et al: "Anti-EGFR monoclonal antibodies in the treatment of non-small cell lung cancer", Annals of Oncology.,vol. 17, No. suppl 2, pp. ii49-ii51, 2006.
Toshiyuki Kozuki: "Skin problems and EGFR-tyrosine kinase inhibitor", Japanese Journal of Clinical Oncology., vol. 46, No. 4, Jan. 29, 2016 (2016-291-298).
Priority Search Report issued by the EPO dated Sep. 8, 2017 for Italian patent application No. IT201700005649.

* cited by examiner

*Primary Examiner* — Bridget E Bunner
*Assistant Examiner* — Fozia M Hamud

(57) ABSTRACT

The present invention refers to compounds of the carotenoid class, such as lycopene or lacto-lycopene, for their use in the treatment and/or prevention of toxicity caused by antitumor drugs, as well as their use in the treatment or remission of tumors in combination with antitumor drugs. Finally, the present invention refers to the combination of the above set forth compounds and drugs with antitumor action.

5 Claims, No Drawings

USE OF CAROTENOID DERIVATIVES TO REDUCE THE TOXICITY AND INCREASE THE EFFICACY OF ANTI-EGFR ANTITUMOR TREATMENTS

This application is a U.S. national stage of PCT/IB2018/050229 filed on 15 Jan. 2018 which claims priority to and the benefit of Italian Application No. 102017000005649 filed on 19 Jan. 2017, the contents of which are incorporated herein by reference in their entireties.

BACKGROUND

The pathway of the epidermal growth factor receptor (EGFR) is one of the main activation routes of the signal in the development of carcinomas. For this reason, the drugs suppressing the activity and/or expression of the EGFR (anti-EGFR drugs) are useful in the therapy of a large number of tumors, such as the lung cancer, the colorectal cancer and the glioblastoma multiforme, as well as for several epithelial tumors.

Several mutations causing primary resistance to treatments with anti-EGFR drugs have been identified. However, despite the identification of such mutations, in a certain percentage of cases wherein the biomolecular characteristics of the tumor could allow to think about positive result of the treatment with anti-EGFR drugs, a resistance to such therapy has been however found.

It is clear that, in these cases, there are activation mechanisms of routes acting in an alternative, complementary or parallel way to that of EGFR, thus allowing the progression of the neoplasm in spite of the pharmacological deactivation of EGFR.

Moreover, the cutaneous and/or mucosal toxicity is a characteristic of these anti-EGFR drugs, which occurs with papulopustular rush, xeroderma, alteration of the piliferous growth, itching, nail alterations and, less frequently, hyperpigmentation, trichomegaly, telangiectasias and mucositis.

The cutaneous toxicity has a key role on the quality of life of the patient, affecting the physical, psychological and social well-being of the individual to such an extent that, in many cases, this leads to the discontinuation or reduction of the dose of the anti-EGFR drug.

For the reasons above, there is the need to find therapeutic solutions which allow to improve the quality of life of patients undergoing a therapy with anti-EFGR drugs (thus acting on the side effects caused by the toxicity of such drugs) and which, if possible, could also improve the efficiency of the antitumor therapy.

OBJECTS OF THE INVENTION

Object of the present invention is the use of a class of compounds in order to reduce the cutaneous and/or mucosal toxicity induced by anti-EGFR drugs.

It is a further object of the present invention the use of the above class of compounds to improve the efficiency of antitumor treatments.

It is also an object of the present invention to provide a combination with pharmacological activity which allows the above described advantages to be obtained, also thanks to synergistic effect of the components of the combination.

DESCRIPTION OF THE INVENTION

Subject-matter of the present invention is a compound selected from the compounds of the carotenoid class, or mixtures thereof, preferably lycopene and/or lacto-lycopene, for use in the prevention, in the relieving, in the improvement, in the decrease, in the therapy and/or in the treatment of the toxicity induced by anti-EGFR drugs, preferably by the monoclonal antibody panitumumab.

In the present invention, "toxicity induced by anti-EGFR drugs" means any toxicity and side effect caused by anti-EGFR drugs, and in particular the cutaneous and/or mucosal toxicity. Manifestations of such cutaneous and/or mucosal toxicity can be, e.g., papulopustular rush, xeroderma, alteration of the piliferous growth, itching, nail alterations, hyperpigmentation, trichomegaly, telangiectasias, mucositis, xeroderma and paronychia.

In the present invention, "anti-EGFR drugs" means all those drugs having effect in the suppression of the activity and/or activation pathway of EGFR, such as for example the monoclonal antibodies targeting the EGFR.

Carotenoids are a class of tetraterpene organic pigments having usually 35-40 carbon atoms in the main chain, and naturally occurring usually within photosynthetic organisms, such as plants and algae.

In particular, lycopene is a compound belonging to the carotenoid class, present in abundance in tomato (*Lycopersicon esculentum*) and derivatives thereof, and possessing the following chemical formula (Formula I):

Formula I

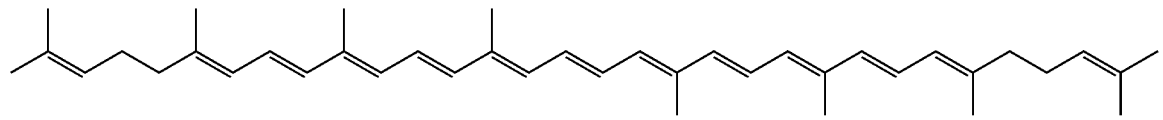

It is widely used in cosmetics, for example within face and body creams to fight against the signs of aging (such as wrinkles, opacity, periorbital dark circles), as a product to treat damaged hair or as protection against UV rays, to be used for example as a cosmetic during periods of longer sun exposure.

Lacto-lycopene is the name conventionally assigned to lycopene formulated with whey proteins. This formulation is created in order to increase the bioavailability of lycopene. Lycopene and lacto-lycopene, as well as carotenoids in general, are intestinally absorbed compounds, in particular in the presence of biliary acids and diet fats. Due to their lipophilicity, once taken they accumulate within the tissues. Thanks to the high number of double bonds, such compounds have high antioxidant activity.

As it will be extensively demonstrated in the experimental section set forth in the following, it has been surprisingly found that the compounds of the carotenoid class, particularly lycopene and lacto-lycopene, have curative and beneficial properties on toxicity caused by anti-EGFR drugs, particularly the monoclonal antibody panitumumab. In order to provide such properties, said compounds can be administered via different routes, and the preferred administration route is the oral route.

The compounds of the carotenoid class, particularly lycopene and lacto-lycopene, can indeed effectively alleviate and decrease the occurrence of side effects, particularly at cutaneous and/or mucosal level, deriving from the suppression of the expression and/or action of EGFR in patients treated with anti-EGFR drugs.

The most common example of such side effects is the cutaneous rash occurring in more than 50% of cases of patients treated with anti-EGFR drugs. Cutaneous rush involves hitching, burning sensations and often pain. Such rush is prevalent in seborrheic areas, i.e. face, scalp and torso, and causes significant discomfort in most of affected patients.

For example, in male patients, there is a frequent impossibility of beard shaving due to the follicular erythematous papules being the cutaneous rush. As a matter of fact, the use of the razor on such papules could lead to evident and painful injuries on the patient's face.

Surprisingly, thanks to the administration of lycopene to male patients of age between 35 and 55 years treated with anti-EGFR drugs, who already presented pustular injuries, significant regression of such injuries has been observed. The regression has been so significant that patients, who could not shave the beard before the treatment with lycopene, could perform normal shaving after 2 weeks from the daily administration of lycopene.

Another example of the side effects caused by anti-EGFR drugs is represented by a diffuse erythema conferring coloration and rosiness on the face of the patient. It should be noted that the rosiness cannot be treated with conventional therapies for the rosacea (chronic dermatosis usually involving the central part of the face).

Surprisingly, it has been noted that the administration of lycopene allows significant regression of the rosiness, and in some patients not yet affected by erythema, it delayed and/or decreased the extension of such coloration.

A further example of a quite diffused toxicity (occurring in about 20% of the patients treated with anti-EGFR drugs) is the paronychia presenting with tumefaction and erythema of the nail fold. Such toxicity can be disabling: in those cases where it is particularly painful, it causes the loss of the function, particularly when it involves the hand nails.

By the administration of lycopene to patients affected by paronychia due to anti-EGFR drugs and with functional disabling of the hand fingers, a resolution of the inflammation and consequently an improvement of the pain condition have been verified, and thanks to this the patients could recover the lost functional ability. Moreover, the treatment with lycopene allowed the patients to recover the normal nail growth and strength.

As previously stated, the cutaneous and mucosal toxicity of anti-EGFR drugs can be so serious to lead to discontinuation or reduction of the dose of the drug itself. In these cases, a fine adjustment of the doses and administration of the anti-EGFR drugs is performed in order to improve as much as possible the quality of life of the patient and, at the same time, to achieve the desired therapeutic effect. Unfortunately, this proper adjustment between the drug effect and the acceptable side effects cannot occur successfully in all cases, thus leading to low quality of life of the patient or, in the worst cases, to therapy failure. Thanks to the use according to the invention and thus to the decrease of the side effects caused by anti-EGFR drugs due to the administration of compounds of the carotenoid class, it will be clearly easier, or even unnecessary, to adjust the proper doses and administration frequencies of anti-EGFR drugs to allow the patient to (i) reach an acceptable quality of life and at the same time (ii) to treat and/or remiss the tumor.

A further subject-matter of the present invention is a compound selected from the compounds of the carotenoid class, or mixtures thereof, preferably lycopene and/or lacto-lycopene, for the use in the antitumor therapy, preferably to be administered in combination with at least one antitumor drug, preferably with at least one anti-EGFR drug, and still more preferably with at least the monoclonal antibody panitumumab.

In the present description, "antitumor therapy" means a therapy which provides the administration of one or more chemical compounds, allowing the treatment and/or remission of tumors, such as for example an antineoplastic chemotherapy.

In the present description, "combination" means that the compound selected from the compounds of the carotenoid class or mixtures thereof, and the at least one antitumor drug, preferably an anti-EGFR drug, and still more preferably the monoclonal antibody panitumumab, can be administered simultaneously and/or via the same administration route, but also and preferably at different times and/or via different administration routes and/or with different administration frequencies, provided that they are administered during the same therapy cycle. An example of such combination is: parenteral administration of panitumumab every 14 days and daily per os lycopene administration, advantageously after meals, for the whole chemotherapy cycle. The preferred administration route for the compound selected from the compounds of the carotenoid class, or mixtures thereof, is the oral route. The doses of the compound selected from the compounds of the carotenoid class, or mixtures thereof, and of the at least one antitumor drug, preferably an anti-EGFR drug, and still more preferably the monoclonal antibody panitumumab, clearly will be selected on the basis of the therapy requirements of the patient.

The actual evidences about the activity of the carotenoids in decreasing the risk of tumor development are significantly conflicting. As a matter of fact, several results of clinical trials present in the art were not able to reliably demonstrate the efficiency of lycopene as compound useful in the prevention of tumor risk; indeed on the 8 Nov. 2005, the Food and Drug Administration (FDA) stated in "Qualified Health Claims: Letter Regarding "Tomatoes and Prostate, Ovarian, Gastric and Pancreatic Cancers (American Longevity Petition)"", as far as lycopene concerned, there are not studies providing information about the reduction of the risk of any specific form of cancer thanks to the lycopene intake.

Moreover carotenoids, and in particular lycopene, have been investigated, according to the known art, mainly as compounds to be introduced in the diet (usually by the intake of foods containing high amounts of them) in order to reduce the risk of carcinogenesis and thus with preventive purpose.

They have neither been studied nor applied as compounds formulated in a pharmaceutical form suitable to be combined with at least one antitumor drug, e.g. an anti-EGFR drug such as panitumumab, in order to obtain higher therapeutic efficiency and/or the remission of an already diagnosed tumor.

As a consequence carotenoids, and particularly lycopene and lacto-lycopene, according to the invention are used to all intents and purposes as antitumor agents within the antineoplastic chemotherapy. Clearly they are preferably used in combination with other antitumor drugs, e.g. with anti- EGFR drugs, as it is a normal procedure for most of the chemotherapies (polychemotherapy).

As it will be clear from the experimental tests performed, it has been thus observed an increase of the antitumor efficiency thanks to the action of the compound selected from the compounds of the carotenoid class, or mixtures thereof in combination with at least one antitumor drug, such as an anti-EGFR drug, e.g. panitumumab. Such increase of the efficiency is in terms of disease control, objective response and stabilization of the disease, as well as in terms of progression-free survival.

It has been surprisingly found that the use according to the invention provides unexpected efficiency due to synergistic effect provided by the compound selected from the carotenoid class, or mixtures thereof, and to the at least one antitumor drug, such as an anti-EGFR drug, e.g. panitumumab. Such synergistic effect is probably due to the ability of the compounds of the carotenoid classes to positively interfere with some pathways involved in the carcinogenesis, by assisting in a synergic way the action of the other antitumor drugs, such as for example the action of an anti-EGFR drug.

This increase of the efficiency is particularly clear in those tumors which can be usually treated with anti-EGFR drugs, and even more in those tumors which, notwithstanding biomolecular features of the cancer itself could allow to think about a positive response of the treatment with anti-EGFR drugs, do not positively respond to such drugs. Examples of such tumors are some forms of the colorectal cancer, or colorectal cancer (CRC).

Finally, subject-matter of the present invention is a combination between a compound selected from the compounds of the carotenoid class, or mixtures thereof, preferably lycopene and/or lacto-lycopene, and at least one antitumor drug, preferably at least one anti-EGFR drug, and still more preferably the monoclonal antibody panitumumab.

The components of the combination according to the invention, as set forth above, can be administered simultaneously and/or via the same administration route, but also and preferably at different times and/or via different administration routes and/or with different administration frequencies, provided that they are administered during the same therapy cycle.

Clearly, the doses of the compound and at least one anti-EGFR drug will be selected on the basis of the therapeutic needs of the patient. By way of example, the administered dose of lycopene is 20 mg.

Thus the combination according to the invention will guarantee the improvement, decrease, prevention, therapy and/or treatment of the toxicity caused by anti-EGFR drugs, particularly of the cutaneous and/or mucosal toxicity, and at the same time it will provide surprising efficiency in the remission and/or therapy of tumors which can be usually treated with anti-EGFR drugs, thanks to the synergistic effect of the compound and anti-EGFR drug of the combination.

EXPERIMENTAL SECTION

Example 1

Protocol of the Clinical Trial

A phase II, prospective, multicentric, randomized (1:1), parallel, double blind study is underway, with the aim of:

evaluating the efficiency of lycopene in reducing the cutaneous and mucosal toxicity induced by panitumumab in patients treated for the metastatic colorectal cancer;

evaluating the efficiency of lycopene in increasing the efficiency of panitumumab in terms of disease control (DC), objective response (OR) and stabilization of disease (SD);

evaluating the efficiency of lycopene versus placebo in improving the efficiency of panitumumab in terms of progression-free survival (PFS).

Example 1.1

Patients

A total of 100 patients have been recruited, 50 in each arm.

The inclusion criteria for the patients in the clinical trial are the following:

age≥18 years;
patients suffering from stage-IV colorectal adenocarcinoma, to whom a treatment with panitumumab is planned;
no previous treatments with anti-EGFR drugs;
presence of at least one unidimensional measurable injury;
no antineoplastic systemic therapy, no experimental therapy, no radiotherapy in the three weeks before the randomization;
written informed consent to join the study;
Performance Status (PS, in accordance with the ECOG scale) 0, 1, 2.

The exclusion criteria for the patients in the clinical trial are the following:

PS>2;
poor patient compliance;
dermatologic diseases in progress that represent a contraindication to the treatment or making difficult the evaluation of the cutaneous toxicity;
presence of clinical conditions which could alter the lycopene absorption (such as for example, altered intestinal tract transit, or malabsorption);
pregnancy;
absence of measurable injuries;
previous treatment with anti-EGFR drugs;
lycopene intolerance.

The recruited patients have been balanced between the two arms based on the different treatment lines (treatment A and treatment B), the sex and recruiting centers, in order to reduce the hormonal influence of the different drugs in combination and the subjective judgement of researchers of the different centers about the cutaneous toxicity and antitumor clinical response.

The patients which should stop the treatment, for the toxicity or inefficacy of the treatment, are however included in the analysis concerning their period of the treatment.

Example 1.2

Treatment

Each arm corresponds to one of the two treatment groups:
treatment A: 6.5 mg lacto-lycopene tablets, 3 tablets/day after dinner (to promote the absorption); and
treatment B: placebo tablets, 3 tablets/day after dinner.

The intake of lycopene or placebo starts the day before the first administration of antitumor agents and goes on with the dosage indicated above until the end of the therapy. The lycopene dosage used for the treatment group A proved to be on the average of those used in various clinical trials carried out in the scope of the different medical areas. At this dosage, lycopene proves to have significant antioxidant effects and not to have relevant side effects. Several studies demonstrated the absence of relevant side effects during the chronic intake of lycopene, with an observed safe level of the intake of such compound up to 75 mg/day doses (OSL=Observed Safe Level).

Even though there are no literature reports about adverse events related to the experimental treatment, possible adverse events due to the intake of lycopene will be monitored for the whole treatment duration and up to a month after its conclusion per each recruited patient.

Both treatment groups, in addition to the A or B treatment set forth above, also receive the normal antitumor therapy for the colorectal carcinoma. Such therapy consists of, as by indication, the administration of panitumumab:
- in first instance in combination with Folfox or Folfiri;
- in second instance in combination with Folfiri or treatments containing Irinotecan;
- in monotherapy in any therapeutic line in patients with resistance to fluoropyrimidines, oxaliplatin and irinotecan, or with intolerance to those drugs.

Standard dosages and timings are used for such kinds of treatments.

In case of temporary interruption of panitumumab due to toxicity, the treatment with lycopene or placebo must go on.

A standardized prophylactic topic treatment, planned for both arms, is also planned starting from the beginning of the experimental treatment:
- cleansing cream base (instead of common soap) for the personal hygiene care;
- mild shampoo (e. g., a shampoo containing colloidal oatmeal);
- aluminum chloride astringent gel (to be applied after making water and salt baths, in case of periungual injuries).

In case of appearance of any cutaneous toxicity of level≥2:
- intake of 100 mg Minocin (minocycline), 1 tablet/day until resolution (i.e., until the achievement of a level=0-1);
- application of topical devices (at clinician's discretion).

Example 1.3

Evaluation Criteria

The evaluation of the cutaneous and mucosal toxicity is carried out every 14 days, at the time of the planned panitumumab administrations. In order to evaluate such toxicity the criteria of the "Multinational Association of Supportive Care in Cancer (MASCC) Skin Toxicity Study Group" have been used (specific criteria for the evaluation of the toxicity due to anti-EGFR drugs). In order to simplify the detection of the cutaneous toxicity, at each access a specific detection form on the cutaneous toxicity is filled, containing the toxicity "level" relative to the different manifestations of cutaneous toxicity expected during the treatment with anti-EGFR drugs. The toxicity is evaluated as follows:
- the worst level of toxicity reached by each patient during the course of the treatment in the two groups (A and B);
- duration of level 3 or level 4 toxicity relative to the duration of the treatment for the individual patient in the two groups;
- number and duration of the antibiotic treatments with Minocin, related to the duration of the treatment for the individual patient;
- toxicity level reached by the patients in the different moments of detection per each clinical manifestation (papulopustular rush, xeroderma, paronychia) in the two groups.

The evaluation of the clinical response to panitumumab treatment is carried out by means of RECIST V1.1 criteria, by parameterizing the images obtained by computed tomography of chest, abdomen and pelvis with contrast medium, performed every about 12 weeks until the disease progression.

The analysis of therapy efficiency for the cutaneous toxicity is performed in accordance with an "intention to treat" approach, i.e. all the randomized patients are included in the analysis and, in case of abandonment or lost at the follow-up for any reason, the patients are considered as patients not reaching the endpoint. However a protocol analysis is carried out as well, by considering only the patients who followed and completed the proposed therapeutic plan.

Example 1.4

Sample Size, Statistical Design of the Study and Data Analysis

The sample size is calculated on the basis of the treatment efficiency against the cutaneous toxicity according to the following hypotheses: (1) a fraction of patients with toxicity level 2-4 in the control arm of 80%; (2) a 30% absolute reduction of toxicity level 2-4 in the experimental arm (3); a 80% potency; (4) a 5% error of type I (two-tailed); (5) a 1:1 ratio of the recruitment in the two arms; (6) a Fisher's exact test to evaluate the differences: therefore it is necessary to recruit 100 patients, calculating a 10% drop-out (90 patients necessary for the evaluation).

The data are evaluated in the following way:
- evaluation of the treatment efficiency versus cutaneous toxicity: Fisher exact test, to evaluate the differences in the percentages with 95% confidence interval (CI);
- evaluation of the clinical efficiency: Fisher exact test, to evaluate the differences in the response percentages with 95% confidence interval; and Kaplan Meier and logrank test, to parametrize the differences of the progression-free survival: HR (95% CI) by Cox regression.

Randomization: randomization blocks, randomization sequence, stratification by center, sex, treatment line.

Example 1.5

| Examination type | Screening (−14 days) | G1 | G15 | G29 | G43 | G57 | G71 | G* | Follow up** |
|---|---|---|---|---|---|---|---|---|---|
| Objective examination | X |  | X | X | X | X | X | X |  |
| Anamnesis | X |  |  |  |  |  |  |  |  |
| ECOG | X | X | X | X | X | X | X | X | X |
| Blood test° | X |  | X | X | X | X | X |  |  |
| Cutaneous evaluation | X |  | X | X | X | X | X | X | X |
| Randomization |  | X |  |  |  |  |  |  |  |

°The blood tests are those carried out routinely, by good medical practice, during the treatment.
G1 day of the first administration of panitumumab and following the day of the first per os administration of lycopene or placebo.
G3 day of the removal of the continuous infusion pump in patients treated with Folfox and Folfiri.
G15, G29, G43, G57, G71 days of the successive administrations of panitumumab.
G* successive administrations of panitumumab with concomitant verification of the cutaneous toxicity every 14 days.
It should be noted that the dermatological evaluation goes on until the interruption of the experimental treatment.
**The follow-up is performed at 30 days from the end of the panitumumab treatment.

Example 2

Results of the Clinical Trial

The clinical trial described by means of the protocol set forth in Example 1 is underway. However, preliminary results concerning both the effect of the treatments to the toxicity caused by anti-EGFR drugs and the clinical efficiency of the treatment to the colorectal cancer are reported.

From preliminary results it is deduced that the cutaneous injuries are less frequently present with respect to the common result during the use of anti-EGFR drugs, more specifically of panitumumab and, in the cases they were present, they manifest themselves with reduced severity in accordance with MASCC criteria.

More specifically, the patients took advantage of an improvement of their quality of life due to a reduction in the frequencies of occurrence and intensity of annoying symptoms, such as itching or cutaneous burning and/or pain at the nail fold of hands and feet which, as described above, can cause disabling functional deficit of such parts of the body.

Moreover, a reduction of the intensity and frequency of the papulopustular erythema has been confirmed, thus allowing a clear decrease of the rosiness taken by the skin of the patients, allowing them less problematic relationships with other people in everyday life, and a reduction of the cases wherein difficulty or impossibility of shaving in the male people has been found, respectively.

Moreover, the need to postpone the administration of the antitumor therapy, which is often required following the onset of high level of cutaneous toxicity, was less frequent. Even though the analyzed sample cannot clarify mechanisms elucidating the increased therapeutic efficiency of the treatment of the tumor diseases due to the combination with the compound of the carotenoid class, or mixtures thereof, such as lacto-lycopene, with respect to the standard oncological therapy, a clear improvement tendency in terms of disease control and PFS (progression-free survival) is inferred from the first collected results.

The invention claimed is:

1. A method of relieving, improving, decreasing and/or treating cutaneous and/or mucosal toxicity induced by at least one anti EGFR drug in patients in need thereof, said method comprising administering to said patients a combination consisting of a compound selected from lycopene and/or lacto-lycopene, or mixtures thereof, and at least one anti EGRF drug causing mucosal and/or cutaneous toxicity.

2. The method according to claim 1, wherein said anti EGFR drug is monoclonal antibody panitumumab.

3. An antitumor therapy comprising administering to patients in need thereof a combination consisting of at least one anti EGRF drug and a compound selected from lycopene and/or lacto-lycopene, or mixtures thereof wherein said lycopene and/or lacto-lycopene or mixtures thereof relieve, improve, decrease and/or treat cutaneous and/or mucosal toxicity induced by said anti EGRF drug.

4. The antitumor therapy according to claim 3 wherein said at least one anti EGRF drug is monoclonal antibody panitumumab.

5. The antitumor therapy according to claim 3 comprising administering to said patients a composition consisting of a compound selected from lycopene and/or lacto-lycopene, or mixtures thereof in combination with at least one anti EGRF drugs causing cutaneous and/or mucosal toxicity.

* * * * *